(12) United States Patent
Yamagata et al.

(10) Patent No.: US 7,276,532 B2
(45) Date of Patent: *Oct. 2, 2007

(54) REMEDIES FOR VESICAL HYPERACTIVITY

(75) Inventors: Tsuyoshi Yamagata, Sunto-gun (JP); Kaoru Atsuki, Sunto-gun (JP); Tetsuji Ohno, Sunto-gun (JP); Shiro Shirakura, Mishima (JP); Akira Karasawa, Sunto-gun (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/472,143

(22) PCT Filed: Mar. 29, 2002

(86) PCT No.: PCT/JP02/03167

§ 371 (c)(1),
(2), (4) Date: Sep. 22, 2003

(87) PCT Pub. No.: WO02/078710

PCT Pub. Date: Oct. 10, 2002

(65) Prior Publication Data
US 2004/0116459 A1  Jun. 17, 2004

(30) Foreign Application Priority Data
Mar. 30, 2001  (JP) .............................. 2001-99801

(51) Int. Cl.
*A61K 31/38* (2006.01)
(52) U.S. Cl. .................................... 514/431
(58) Field of Classification Search ............... 514/431, 514/291, 375
See application file for complete search history.

(56) References Cited

U.S. PATENT DOCUMENTS 5,726,325 A  3/1998 Yoshida et al. ............... 549/48

6,211,227 B1  4/2001 Yoshida et al. ............. 514/431

FOREIGN PATENT DOCUMENTS

WO  97/14672  4/1997
WO  98/46587  10/1998

OTHER PUBLICATIONS

Yoshimura, et al., "Increased Excitability of Afferent Neurons Innervating Rat Urinary Bladd r after Chronic Bladder Inflammation", *The Journal of Neuroscience*, (1999), vol. 19, No. 11, pp. 4644-4653.
Yoshimura, Bladder Afferent Pathway and Spinal Cord Injury: Possible Mechanisms Inducing Hyperreflexica of the Urinary Bladder, *Progress in Neurobiology*, vol. 57, (1999), pp. 583-606.

*Primary Examiner*—Raymond J. Henley, III
(74) *Attorney, Agent, or Firm*—Fitzpatrick, Cella, Harper & Scinto

(57) ABSTRACT

The present invention provides a therapeutic agent for overactive bladder comprising, as an active ingredient, a tricyclic compound represented by formula (I):

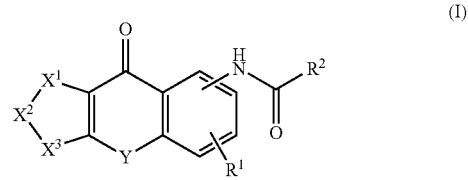

[wherein $R^1$ represents a hydrogen atom, substituted or unsubstituted lower alkyl, and the like;
$X^1$—$X^2$—$X^3$ represents $CR^5$=$CR^6$—$CR^7$=$CR^8$, $CR^5$=$CR^6$—S, and the like;
Y represents —$CH_2S$—, —$SOCH_2$—, and the like; and
$R^2$ represents a hydrogen atom, and the like] or a pharmaceutically acceptable salt thereof.

4 Claims, No Drawings

REMEDIES FOR VESICAL HYPERACTIVITY

TECHNICAL FIELD

The present invention relates to a therapeutic agent for overactive bladder.

BACKGROUND ART

Overactive bladder is a pathological condition observed in patients showing symptoms such as urinary urgency or urinary frequency. Some patients with overactive bladder show urinary urge incontinence and others do not. Micturition reflex is physiologically controlled by the complex reflex pathways including peripheral and central nervous systems [Urology, Vol. 50, Supplement No. 6A, pp. 36-52 (1997)]. "Urinary urgency" refers to a sudden and strong desire to void, and "urinary urge incontinence" refers to involuntary urinary leakage associated with urinary urgency.

In patients suffering from the symptoms such as urinary urgency and urinary urge incontinence due to overactive bladder, involuntary (uninhibited) contraction of the detrusor muscle is frequently observed in a cystometric measurement, and it is called detrusor overactivity. This detrusor overactivity is considered to be a main cause of urinary urgency and also of urinary urge incontinence, and urinary urgency can lead to urinary frequency. The detrusor overactivity is called neurogenic bladder (detrusor hyperreflexia) when a neurologic problem is found in a patient, and unstable bladder (detrusor instability) when a neurologic problem is not found. Unstable bladder is considered to be due to potential neurogenic bladder or the disorder of the bladder smooth muscle per se (or both of them). Examples of neurologic problems relating to neurogenic bladder includes Parkinson's disease, stroke, diabetes, multiple sclerosis, neuropathy, spinal injury, etc.

Tricyclic compounds having the activity to prolong the intervals of bladder contractions and pharmaceutically acceptable salts thereof are known as therapeutic agents for urinary incontinence (WO97/14672 and WO98/46587). However, it is not known that the compound groups inhibit overactive bladder.

DISCLOSURE OF THE INVENTION

The present invention relates to the following (1) to (27).
(1) A therapeutic agent for overactive bladder comprising, as an active ingredient, a tricyclic compound represented by formula (I):

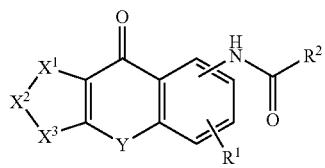

(I)

[wherein $R^1$ represents a hydrogen atom, substituted or unsubstituted lower alkyl, substituted or unsubstituted lower alkoxy or halogen;
$X^1$—$X^2$—$X^3$ represents $CR^5$=$CR^6$—$CR^7$=$CR^8$ (wherein $R^5$, $R^6$, $R^7$ and $R^8$, which may be the same or different, each represent a hydrogen atom, substituted or unsubstituted lower alkyl, hydroxy, substituted or unsubstituted lower alkoxy, nitro, amino, mono(lower alkyl)-substituted amino, di (lower alkyl)-substituted amino, substituted or unsubstituted lower alkanoylamino or halogen), $N(O)_m$=$CR^6$—$CR^7$=$CR^8$ (wherein $R^6$, $R^7$ and $R^8$ have the same significances as defined above, respectively, and m represents 0 or 1), $CR^5$=$CR^6$—$N(O)_m$=$CR^8$ (wherein $R^5$, $R^6$, $R^8$ and m have the same significances as defined above, respectively), $CR^5$=$CR^6$—$CR^7$=$N(O)_m$ (wherein $R^5$, $R^6$, $R^7$ and m have the same significances as defined above, respectively), $CR^5$=$CR^6$—O (wherein $R^5$ and $R^6$ have the same significances as defined above, respectively), $CR^5$=$CR^6$—S (wherein $R^5$ and $R^6$ have the same significances as defined above, respectively), O—$CR^7$=$CR^8$ (wherein $R^7$ and $R^8$ have the same significances as defined above, respectively) S—$CR^7$=$CR^8$ (wherein $R^7$ and $R^8$ have the same significances as defined above, respectively) or O—$CR^7$=N (wherein $R^7$ has the same significance as defined above);
Y represents —$CH_2S$—, —$CH_2SO$—, —$CH_2SO_2$—, —$CH_2O$—, —CH=CH—, —$(CH_2)_p$— (wherein p represents an integer of 0 to 2), —$SCH_2$—, —$SOCH_2$—, —$SO_2CH_2$— or —$OCH_2$—; and
$R^2$ represents a hydrogen atom, substituted or unsubstituted lower alkyl, substituted or unsubstituted lower alkenyl, substituted or unsubstituted lower alkoxy, amino, mono(substituted or unsubstituted lower alkyl)-substituted amino, di(substituted or unsubstituted lower alkyl)—substituted amino, substituted or unsubstituted aryl, substituted or unsubstituted heteroaryl, substituted or, unsubstituted aralkylamino, substituted or unsubstituted arylamino or a substituted or unsubstituted heteroalicyclic group] or a pharmaceutically acceptable salt thereof.

(2) A therapeutic agent for overactive bladder comprising, as an active ingredient, a tricyclic compound represented by formula (Ia):

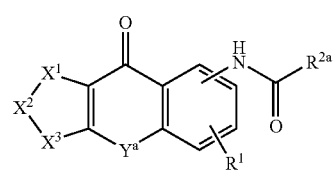

(Ia)

[wherein $R^1$ and $X^1$—$X^2$—$X^3$ have the same significances as defined above, respectively;
$Y^a$ represents —$CH_2SO_2$—, —$SCH_2$—, —$SOCH_2$—, —$SO_2CH_2$— or —$OCH_2$—; and
when $Y^a$ is —$CH_2SO_2$—, —$SCH_2$—, —$SOCH_2$— or —$SO_2CH_2$—,
$R^{2a}$ represents a hydrogen atom, substituted or unsubstituted lower alkyl, substituted or unsubstituted lower alkenyl, trifluoromethyl, substituted or unsubstituted lower alkoxy, amino, mono(substituted or unsubstituted lower alkyl)-substituted amino, di(substituted or unsubstituted lower alkyl)-substituted amino, substituted or unsubstituted aryl, substituted or unsubstituted heteroaryl, substituted or unsubstituted aralkylamino, substituted or unsubstituted arylamino, a substituted- or unsubstituted heteroalicyclic group or formula (II):

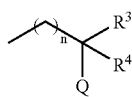

(II)

(wherein n is 0 or 1; $R^3$ and $R^4$, which may be the same or different, each represent a hydrogen atom, substituted or unsubstituted lower alkyl, substituted or unsubstituted cycloalkyl, substituted or unsubstituted aryl, substituted or unsubstituted aralkyl or trifluoromethyl, or $R^3$ and $R^4$ may be combined together with the adjacent carbon atom to form cycloalkyl; and Q represents hydroxy, substituted or unsubstituted lower alkoxy, amino or halogen)., and when $Y^a$ is —OCH$_2$—, $R^{2a}$ represents a hydrogen atom, substituted or unsubstituted lower alkenyl, trifluoromethyl, substituted or unsubstituted lower alkoxy, amino, mono(substituted or unsubstituted lower alkyl)-substituted amino, di(substituted or unsubstituted lower alkyl)-substituted amino, substituted or unsubstituted aryl, substituted or unsubstituted heteroaryl, substituted or unsubstituted aralkylamino, substituted or unsubstituted arylamino, a substituted or unsubstituted heteroalicyclic group or formula (II):

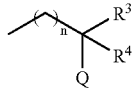

(II)

(wherein n, $R^3$, $R^4$ and Q have the same significances as defined above, respectively)] or a pharmaceutically acceptable salt thereof.

(3) The therapeutic agent for overactive bladder comprising, as an active ingredient, a tricyclic compound or a pharmaceutically acceptable salt thereof according to (2), wherein $Y^a$ is —CH$_2$SO$_2$—, —SCH$_2$—, —SOCH$_2$— or —SO$_2$CH$_2$—.

(4) The therapeutic agent for overactive bladder comprising, as an active ingredient, a tricyclic compound or a pharmaceutically acceptable salt thereof according to (2), wherein $Y^a$ is —OCH$_2$—.

(5) The therapeutic agent for overactive bladder comprising, as an active ingredient, a tricyclic compound or a pharmaceutically acceptable salt thereof according to any of (2) to (4), wherein $R^1$ is a hydrogen atom, substituted or unsubstituted lower alkoxy or halogen.

(6) The therapeutic agent for overactive bladder comprising, as an active ingredient, a tricyclic compound or a pharmaceutically acceptable salt thereof according to any of (2) to (4), wherein $R^1$ is a hydrogen atom.

(7) The therapeutic agent for overactive bladder comprising, as an active ingredient, a tricyclic compound or a pharmaceutically acceptable salt thereof according to any of (2), (5) and (6), wherein $Y^a$ is —CH$_2$SO$_2$—, —SO$_2$CH$_2$— or —OCH$_2$—.

(8) The therapeutic agent for overactive bladder comprising, as an active ingredient, a tricyclic compound or a pharmaceutically acceptable salt thereof according to any of (2), (5) and (6), wherein $Y^a$ is —CH$_2$SO$_2$— or —SO$_2$CH$_2$—.

(9) The therapeutic agent for overactive bladder comprising, as an active ingredient, a tricyclic compound or a pharmaceutically acceptable salt thereof according to any of (2), (5) and (6), wherein $Y^a$ is —CH$_2$SO$_2$—.

(10) The therapeutic agent for overactive bladder comprising, as an active ingredient, a tricyclic compound or a pharmaceutically acceptable salt thereof according to any of (2) to (9), wherein $X^1$—$X^2$—$X^3$ is S—CR$^7$=CR$^8$ (wherein $R^7$ and $R^8$ have the same significances as defined above, respectively).

(11) The therapeutic agent for overactive bladder comprising, as an active ingredient, a tricyclic compound or a pharmaceutically acceptable salt thereof according to any of (2) to (9), wherein $X^1$—$X^2$—$X^3$ is CR$^5$=CR$^6$—CR$^7$=CR$^8$ (wherein $R^5$, $R^6$, $R^7$ and $R^8$ have the same significances as defined above, respectively).

(12) The therapeutic agent for overactive bladder comprising, as an active ingredient, a tricyclic compound or a pharmaceutically acceptable salt thereof according to any of (2) to (11), wherein $R^{2a}$ is formula (II):

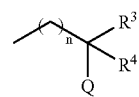

(II)

(wherein n, $R^3$, $R^4$ and Q have the same significances as defined above, respectively).

(13) The therapeutic agent for overactive bladder comprising, as an active ingredient, a tricyclic compound or a pharmaceutically acceptable salt thereof according to (12), wherein n is 0.

(14) The therapeutic agent for overactive bladder comprising, as an active ingredient, a tricyclic compound or a pharmaceutically acceptable salt thereof according to (13), wherein $R^3$ is methyl, $R^4$ is trifluoromethyl, and Q is hydroxy.

(15) The therapeutic agent for overactive bladder comprising, as an active ingredient, a tricyclic compound or a pharmaceutically acceptable salt thereof according to (2), wherein $R^1$ is a hydrogen atom, $Y^a$ is —CH$_2$SO$_2$—, $X^1$—$X^2$—$X^3$ is S—CR$^7$=CR$^8$ (wherein $R^7$ and $R^8$ have the same significances as defined above, respectively), and $R^2$ is formula (III):

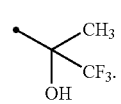

(III)

(16) A therapeutic agent for overactive bladder comprising, as an active ingredient, a tricyclic compound represented by formula (Ib):

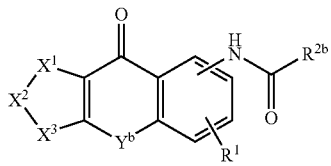

(IIb)

[wherein $R^1$ and $X^1$—$X^2$—$X^3$ have the same significances as defined above, respectively;
$Y^b$ represents —$CH_2O$—, —$CH_2S$—, —$CH_2SO$—, —CH=CH— or —$(CH_2)_p$— (wherein p has the same significance as defined above); and $R^{2b}$ represents formula (III):

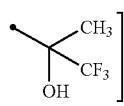

(III)

or a pharmaceutically acceptable salt thereof.

(17) The therapeutic agent for overactive bladder comprising, as an active ingredient, a tricyclic compound or a pharmaceutically acceptable salt thereof according to (16), wherein $X^1$—$X^2$—$X^3$ is $CR^5$=$CR^6$—$CR^7$=$CR^8$ (wherein $R^5$, $R^6$, $R^7$ and $R^8$ have the same significances as defined above, respectively) or $CR^5$=$CR^6$—$CR^7$=N (wherein $R^5$, $R^6$ and $R^7$ have the same significances as defined above, respectively).

(18) The therapeutic agent for overactive bladder comprising, as an active ingredient, a tricyclic compound or a pharmaceutically acceptable salt thereof according to (16), wherein $X^1$—$X^2$—$X^3$ is $CR^5$=$CR^6$—O (wherein $R^5$ and $R^6$ have the same significances as defined above, respectively) or $CR^5$=$CR^6$—S (wherein $R^5$ and $R^6$ have the same significances as defined above, respectively).

(19) The therapeutic agent for overactive bladder comprising, as an active ingredient, a tricyclic compound or a pharmaceutically acceptable salt thereof according to (16), wherein $X^1$—$X^2$—$X^3$ is O—$CR^7$=$CR^8$ (wherein $R^7$ and $R^8$ have the same significances as defined above, respectively) or S—$CR^7$=$CR^8$ (wherein $R^7$ and $R^8$ have the same significances as defined above, respectively).

(20) The therapeutic agent for overactive bladder comprising, as an active ingredient, a tricyclic compound or a pharmaceutically acceptable salt thereof according to any of (16) to (19), wherein $Y^b$ is —$CH_2O$—.

(21) The therapeutic agent for overactive bladder comprising, as an active ingredient, a tricyclic compound or a pharmaceutically acceptable salt thereof according to any of (16) to (19), wherein $Y^b$ is —$(CH_2)_p$— (wherein p has the same significance as defined above).

(22) The therapeutic agent for overactive bladder comprising, as an active ingredient, a tricyclic compound or a pharmaceutically acceptable salt thereof according to (21), wherein p is 0.

(23) The therapeutic agent for overactive bladder comprising, as an active ingredient, a tricyclic compound or a pharmaceutically acceptable salt thereof according to (21), wherein p is 2.

(24) The therapeutic agent for overactive bladder comprising, as an active ingredient, a tricyclic compound or a pharmaceutically acceptable salt thereof according to any of (16) to (19), wherein $Y^b$ is —CH=CH—.

(25) The therapeutic agent for overactive bladder comprising, as an active ingredient, a tricyclic compound or a pharmaceutically acceptable salt thereof according to any of (16) to (19), wherein $Y^b$ is —$CH_2S$— or —$CH_2SO$—.

(26) Use of the tricyclic compound or the pharmaceutically acceptable salt thereof according to any of (1) to (25) for the production of a therapeutic agent for overactive bladder.

(27) A method for treating overactive bladder, comprising a step of administering an effective amount of the tricyclic compound or the pharmaceutically acceptable salt thereof according to any of (1) to (25).

Hereinafter, the compounds represented by formula (I) are referred to as Compounds (I), and the same applies to the compounds of other formula numbers.

In the definitions of the groups in formula (I), the lower alkyl moiety of the lower alkyl, the lower alkoxy, the mono(lower alkyl)-substituted amino and the di(lower alkyl)-substituted amino includes straight-chain or branched lower alkyl groups having 1 to 8 carbon atoms, such as methyl, ethyl, propyl, isopropyl, butyl, isobutyl, sec-butyl, tert-butyl, pentyl, hexyl, 1,2,2-trimethylpropyl, heptyl and octyl. The two lower alkyl moieties of the di(lower alkyl)-substituted amino may be the same or different.

The lower alkanoyl moiety of the lower alkanoylamino includes lower alkanoyl groups having 1 to 6 carbon atoms, such as formyl, acetyl, propanoyl, butanoyl, pentanoyl, 2,2-dimethylpropanoyl and hexanoyl.

The lower alkenyl includes straight-chain or branched lower alkenyl groups having 2 to 6 carbon atoms, such as vinyl, allyl, 1-propenyl, methacryl, 1-butenyl, crotyl, pentenyl and hexenyl.

The aryl and the aryl moiety of the arylamino include aryl groups having 6 to 14 carbon atoms, such as phenyl, naphthyl and anthranyl.

The heteroaryl includes 5- or 6-membered monocyclic heteroaromatic groups containing at least one atom selected from the group consisting of a nitrogen atom, an oxygen atom and a sulfur atom, and bicyclic or tricyclic condensed heteroaromatic groups in which 3- to 8-membered rings are condensed and which contain at least one atom selected from the group consisting of a nitrogen atom, an oxygen atom and a sulfur atom. Specific examples are pyridyl, furyl, thienyl, quinolyl, imidazolyl, benzimidazolyl, thiazolyl, pyrazinyl, pyrimidinyl, pyridazinyl, isoquinolinyl, phthalazinyl, quinazolinyl, quinoxalinyl, naphthyridinyl, cinnolinyl, pyrrolyl, pyrazolyl, triazolyl, tetrazolyl, oxazolyl, indolyl, benzotriazolyl, benzothiazolyl, benzoxazolyl, purinyl, and the like.

The aralkyl moiety of the aralkylamino includes aralkyl groups having 7 to 12 carbon atoms, such as benzyl, phenethyl and naphthylmethyl.

The heteroalicyclic group includes 3- to 8-membered monocyclic heteroalicyclic groups containing at least one atom selected from the group consisting of a nitrogen atom, an oxygen atom and a sulfur atom, and bicyclic or tricyclic condensed heteroalicyclic groups in which 3- to 8-membered rings are condensed and which contain at least one atom selected from the group consisting of a nitrogen atom, an oxygen atom and a sulfur atom. Specific examples are tetrahydropyridinyl, tetrahydroquinolinyl, tetrahydroisoquinolinyl, tetrahydropyranyl, tetrahydrofuranyl, dihydrobenzofuranyl, pyrrolidinyl, piperidino, piperidyl, perhydroazepinyl, perhydroazocinyl, morpholino, morpholinyl, thiomorpholino, thiomorpholinyl, piperazinyl, homopiperidino, homopiperazinyl, dioxolanyl, imidazolidinyl, imidazolinyl, pyrazolidinyl, indolinyl, isoindolinyl, pyrrolinyl, pyrrolidonyl, piperidonyl, perhydroazepinonyl, thiazolidonyl, oxazolidonyl, succinimido, phthalimido, glutarimido, maleimido, hydantoinyl, thiazolidinedionyl, oxazolidinedionyl, tetrahydrothienyl, chromanyl, pipecolinyl, and the like.

The halogen means a fluorine, chlorine, bromine or iodine atom.

The substituted lower alkyl, the substituted lower alkoxy, the mono(substituted lower alkyl)-substituted amino, the di(substituted lower alkyl)-substituted amino, the substituted lower alkanoylamino and the substituted lower alkenyl each have 1 to a substitutable number (preferably 1 to 6, more preferably 1 to 4) of substituents which are the same or different. Examples of the substituents are hydroxy, halogen, nitro, amino, carboxy, mono(lower alkyl)-substituted amino, di(lower alkyl)-substituted amino, lower alkoxy, cycloalkyl, substituted cycloalkyl [the substituted cycloalkyl has 1 to 3 substituents which are the same or different, such as hydroxy, halogen, nitro, amino, mono (lower alkyl)-substituted amino, di(lower alkyl)-substituted amino or lower alkoxy], aryl, substituted aryl (the substituent in the substituted aryl has the same significance as that in the substituted aryl described below), aralkyl, substituted aralkyl (the substituent in the substituted aralkyl has the same significance as that in the substituted aralkyl described below), substituted lower alkoxy [the substituted lower alkoxy has 1 to 3 substituents which are the same or different, such as hydroxy, halogen, nitro, amino, mono (lower alkyl)-substituted amino, di(lower alkyl)-substituted amino or lower alkoxy], and the like. In the above, the cycloalkyl may be bound to the substituted lower alkyl by spiro-union. Herein, the halogen has the same significance as defined above, the lower alkyl moiety of the mono(lower alkyl)-substituted amino, the di(lower alkyl)-substituted amino and the lower alkoxy has the same significance as the above-described lower alkyl, and the aryl has the same significance as defined above. The cycloalkyl includes cycloalkyl groups having 3 to 8 carbon atoms, such as cyclopropyl, cyclobutyl, cyclopentyl, cyclohexyl, cycloheptyl and cyclooctyl. The aralkyl includes aralkyl groups having 7 to 12 carbon atoms, such as benzyl, phenethyl and naphthylmethyl.

The substituted aryl, the substituted heteroaryl, the substituted aralkylamino and the substituted arylamino each have 1 to 3 substituents which are the same or different. Examples of the substituents are lower alkyl, hydroxy, amino, halogen, and the like, and the lower alkyl and the halogen have the same significances as defined above, respectively.

The substituted heteroalicyclic group has 1 to 3 substituents which are the same or different. Examples of the substituents are lower alkyl, hydroxy, halogen, and the like, and the lower alkyl and the halogen have the same significances as defined above, respectively.

In the definitions of formula (Ia) and formula (Ib), the lower alkyl moiety of the lower alkyl, the lower alkoxy, the mono(lower alkyl)-substituted amino and the di(lower alkyl)-substituted amino includes straight-chain or branched lower alkyl groups having 1 to 6 carbon atoms, such as methyl, ethyl, propyl, isopropyl, butyl, isobutyl, sec-butyl, tert-butyl, pentyl, hexyl and 1,2,2-trimethylpropyl. The two lower alkyl moieties of the di(lower alkyl)-substituted amino may be the same or different.

The halogen, the lower alkenyl, the aryl moiety of the aryl and the arylamino, the heteroaryl, the aralkyl moiety of the aralkyl and the aralkylamino, the heteroalicyclic group and the cycloalkyl respectively have the same significances as the halogen, the lower alkenyl, the aryl, the heteroaryl, the aralkyl, the heteroalicyclic group and the cycloalkyl in the definitions of the groups in formula (I) or in the definitions of the substituents in the definitions of the groups in formula (I).

The substituted lower alkyl, the substituted lower alkoxy, the mono(substituted lower alkyl)-substituted amino, the di(substituted lower alkyl)-substituted amino, the substituted lower alkenyl and the substituted cycloalkyl each have 1 to 3 substituents which are the same or different. Examples of the substituents are hydroxy, halogen, nitro, amino, carboxy, mono(lower alkyl)-substituted amino, di(lower alkyl)-substituted amino, lower alkoxy, and the like. The halogen has the same significance as defined above, and the lower alkyl moiety of the mono(lower alkyl)-substituted amino, the di(lower alkyl)-substituted amino and the lower alkoxy has the same significance as the above-described lower alkyl.

The substituted aryl, the substituted heteroaryl, the substituted aralkyl, the substituted aralkylamino and the substituted arylamino each have 1 to 3 substituents which are the same or different. Examples of the substituents are lower alkyl, hydroxy, amino, halogen, and the like, and the lower alkyl and the halogen have the same significances as defined above, respectively.

The substituted heteroalicyclic group has 1 to 3 substituents which are the same or different. Examples of the substituents are lower alkyl, hydroxyl, halogen, and the like, and the lower alkyl and the halogen have the same significances as defined above, respectively.

The pharmaceutically acceptable salts of Compound (I), Compound (Ia) and Compound (Ib) include pharmaceutically acceptable acid addition salts, metal salts, ammonium salts, organic amine addition salts and amino acid addition salts. Examples of the acid addition salts are inorganic acid addition salts such as hydrochloride, hydrobromide, hydroiodide, nitrate, sulfate and phosphate, and organic acid addition salts such as formate, acetate, benzoate, maleate, fumarate, succinate, tartrate, citrate, oxalate, glyoxylate, methanesulfonate, ethanesulfonate, benzenesulfonate and lactate. Examples of the metal salts are alkali metal salts such as a lithium salt, a sodium salt and a potassium salt, alkaline earth metal salts such as a magnesium salt and a calcium salt, an aluminum salt, a zinc salt, and the like. Examples of the ammonium salts are ammonium, tetramethylammonium, and the like. Examples of the organic amine addition salts are salts with morpholine, piperidine, or the like, and examples of the amino acid addition salts are salts with glycine, phenylalanine, aspartic acid, glutamic acid, lysine, or the like.

The tricyclic compounds used in the present invention can be produced according to the methods disclosed in the above publications or similar methods, and can be isolated and purified by purification methods conventionally used in synthetic organic chemistry, for example, neutralization, filtration, extraction, washing, drying, concentration, recrystallization and various kinds of chromatography.

When it is desired to obtain a salt of the tricyclic compound used in the present invention, in the case where it is produced in the form of the salt, it can be subjected to purification as such, and where it is produced in the form of a free base, it can be converted into a salt, after being dissolved or suspended in a suitable solvent, by adding an acid or a base thereto.

There may be optical isomers for some of the tricyclic compounds used in the present invention. All possible stereoisomers and mixtures thereof can be used as active ingredients of the therapeutic agent of the present invention.

The tricyclic compounds or pharmaceutically acceptable salts thereof used in the present invention may exist in the form of adducts with water or various solvents, which can also be used as active ingredients of the therapeutic agent of the present invention.

Specific examples of Compounds (I) are illustrated below.

Compound 1

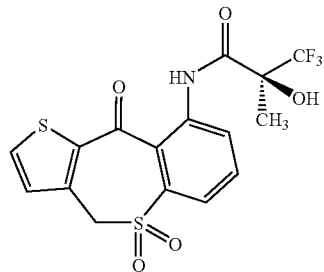

Compound 2

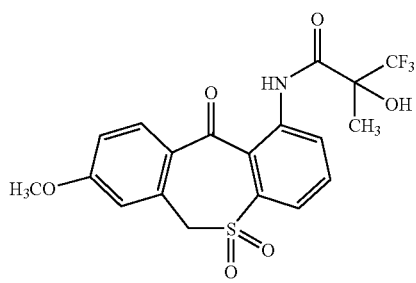

Compound 3

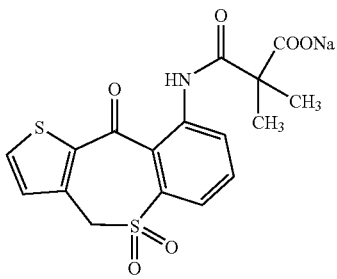

Compound 4

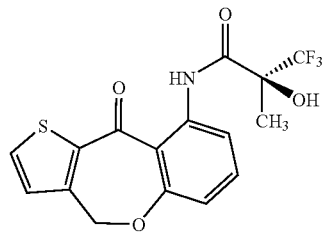

-continued

Compound 5

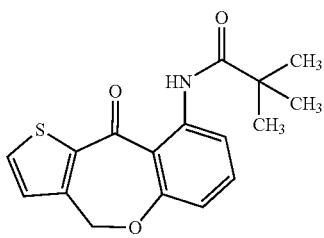

Compound 6

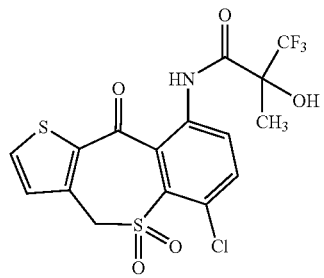

Compound 1 is the same compound as Compound (1-25) described in WO98/46587, Compound 2 is the same compound as Compound (1-24) described in WO98/46587, Compound 4 is the same compound as Compound 7 described in WO97/14672, and Compound 6 is the same compound as Compound (1-33) described in WO98/46587. Compounds 3 and 5 can be produced according to the method described in WO97/14672 or WO98/46587.

The pharmacological activities of typical Compounds (I) are described in test examples.

TEST EXAMPLE 1

Inhibitory Activity on Detrusor Hyperreflexia

The experiment was carried out according to the method of Cheng, et al. [Brain Res., Vol. 678, pp. 40-48 (1995)].

Female SD rats of 8 to 10 weeks of age (supplied by Japan SLC) were used in the test. Five to seven animals of these rats were put in each metal cage and reared by allowing them to freely take commercially available chow and water, in an animal room at room temperature between 19 and 25° C. and humidity between 30 and 70% under illumination for 12 hours (from 7:00 a.m. to 7:00 p.m.) per day.

An operation of spinal cord injury was performed in the rats. Each animal was anesthetized with diethyl ether and the skin of the back side thoracic cord part was incised. A laminectomy at the 7th to 8th thoracic vertebrae level was performed. Then, the thoracic cord at the T7-T8 segments was macroscopically cut and a section of spinal cord (about 5 mm) was removed, and the wound cavity of the removed part was filled with oxidized regenerated cellulose for hemostasis. The incised part was sutured with a surgical silk. After the spinal cord injury operation, urine was expressed manually twice per day (at 8:00-9:00 and 18:00-19:00) for about 3 weeks until autonomic micturition developed. An antibiotic (ampicillin, Sigma. Chemical Co.) was intramuscularly administered to the animals at a dose of 150 mg/kg once to twice per day for about 2 weeks.

Four to five weeks after the spinal cord injury, the rats were subjected to bladder catheterization. Under diethyl ether anesthesia, the bladder was exposed by midline incision of the abdomen. A polyethylene tube (PE-50, Nippon Becton Dickinson Co., Ltd.), which had a blunt end to protect tissue from injury, was filled with a physiological saline (Otsuka Pharmaceutical Co., Ltd.) and inserted from the bladder apex. The bladder catheter was fixed with a surgical silk ligature and indwelled. The other end of the catheter was exposed subcutaneously from the back of the neck, plugged and then fixed to the skin with a surgical thread.

Four to six days after the bladder catheterization, a cystometry test was performed. The rats were put in a Bollman cage (Natsume Seisakusho Co., Ltd.) and a three-way cock was connected to the bladder catheter, one end of the cock was connected to a pressure transducer (Nihon Kohden Corp.) and the other end was connected to a 50-mL syringe (Terumo Corp.) arranged to an infusion pump (Harvard Apparatus, Inc.) for physiological saline infusion. The intravesical pressure signal from the pressure transducer was amplified with a strain pressure amplifier (AP-601G, Nihon Kohden Corp.) connected thereto, and was recorded on a thermal array recorder (RTA-1200, Nihon Kohden Corp.) via a polygraph system (RMP-6008, Nihon Kohden Corp.) containing the above amplifier. Sixty to ninety minutes after the completion of the preparation for the measurement, a room temperature physiological saline was infused into the bladder at a flow rate of 10 mL/h for 30 minutes, the occurence of micturition contractions was confirmed. Thirty minutes later, the infusion of physiological saline was carried out again for 30 minutes, and the intravesical pressure was measured to be used as the pre-administration value. Each of Compounds 1 to 6 was suspended in a 0.5 w/v % aqueous solution of methylcellulose at a concentration of 1 mg/mL suspension. The suspension was further diluted with a 0.5 w/v % aqueous solution of methylcellulose to prepare a suspension or solution for the administration at the intended concentration, which was then orally administered to the animals at a volume of 1 mL/kg. The period of 1, 3 and 5 hours after the dosing was used as the measuring time after the administration of the solvent or a compound tested, and the intravesical infusion of a physiological saline was carried out during a duration of 15 minutes around each measuring time (i.e. from 45 to 75 minutes, from 165 to 195 minutes and from 285 to 315 minutes after the administration of the compound).

Micturition contraction was measured as an index of the voiding function and pre-micturition contraction was measured as an index of detrusor hyperreflexia. The average for all micturition contraction values observed during each 30-minute measurement period and the average of the maximum pre-micturition contraction between respective micturition contractions were respectively regarded as the amplitude of micturition contractions and pre-micturition contractions at each measurement point. The values of both contractions were read from intravesical pressure waveforms recorded on a chart paper using a digitizer (KD3220, Graphtec Corporation) controlled by a computer (PC-9801NS/R, NEC), and saved as a WJ2 file on Lotus 1-2-3 R2.5J (Lotus). The WJ2 file was taken into Excel for Windows version 7.0 (Microsoft). The amplitude of pre-micturition contractions and micturition contractions were expressed as relative values when the values before the drug administration that were defined as 100, and the average±standard error was calculated for each group.

The values (%) of pre-micturition contractions after the administration of the solvent or compound are shown in Table 1 and the values (%) of micturition contractions are shown in Table 2.

TABLE 1

|  | | Compound 1 (mg/kg, p.o.) | | |
|---|---|---|---|---|
|  | Control | 0.001 | 0.01 | 0.1 |
| Before administration | 100.0 ± 0.0 | 100.0 ± 0.0 | 100.0 ± 0.0 | 100.0 ± 0.0 |
| After 1 hr. | 115.0 ± 12.1 | 83.5 ± 6.8 | 59.6 ± 8.1* | 52.3 ± 9.1* |
| After 3 hrs. | 128.4 ± 21.5 | 95.4 ± 12.0 | 51.2 ± 6.7* | 33.3 ± 6.3* |
| After 5 hrs. | 120.2 ± 24.5 | 105.5 ± 20.8 | 42.2 ± 7.2* | 28.5 ± 6.2* |

|  | Control | Compound 2 (mg/kg, p.o.) 3 |
|---|---|---|
| Before administration | 100.0 ± 0.0 | 100.0 ± 0.0 |
| After 1 hr. | 124.0 ± 16.1 | 55.1 ± 7.3 |
| After 3 hrs. | 93.7 ± 12.8 | 80.2 ± 23.6 |
| After 5 hrs. | 97.7 ± 8.8 | 66.8 ± 14.5 |

|  | Control | Compound 3 (mg/kg, p.o.) 1 |
|---|---|---|
| Before administration | 100 ± 0.0 | 100.0 ± 0.0 |
| After 1 hr. | 116.7 ± 11.0 | 66.2 ± 15.8 |
| After 3 hrs. | 151.9 ± 43.2 | 65.3 ± 24.9 |
| After 5 hrs. | 139.2 ± 40.3 | 52.3 ± 13.7 |

|  | Control | Compound 4 (mg/kg, p.o.) 1 |
|---|---|---|
| Before administration | 100.0 ± 0.0 | 100 |
| After 1 hr. | 101.3 ± 10.6 | 58.6 |
| After 3 hrs. | 115.3 ± 17.0 | 44.4 |
| After 5 hrs. | 98.8 ± 19.3 | 42.6 |

TABLE 1-continued

|  | Control | Compound 5 (mg/kg, p.o.) 1 |
|---|---|---|
| Before administration | 100.0 ± 0.0 | 100.0 ± 0.0 |
| After 1 hr. | 124.2 ± 16.1 | 86.2 ± 10.2 |
| After 3 hrs. | 93.7 ± 12.8 | 57.3 ± 9.2 |
| After 5 hrs. | 97.7 ± 8.8 | 44.8 ± 6.1 |

|  | Control | Compound 6 (mg/kg, p.o.) 1 |
|---|---|---|
| Before administration | 100.0 ± 0.0 | 100.0 ± 0.0 |
| After 1 hr. | 92.1 ± 11.1 | 62.7 ± 9.3 |
| After 3 hrs. | 95.4 ± 15.1 | 87.9 ± 16.9 |
| After 5 hrs. | 90.8 ± 11.1 | 69.0 ± 11.8 |

*$p < 0.05$ (Comparison with the control group)
(n = 5-6: Dunnet test)

TABLE 2

|  |  | Compound 1 (mg/kg, p.o.) | | |
|---|---|---|---|---|
|  | Control | 0.001 | 0.01 | 0.1 |
| Before administration | 100.0 ± 0.0 | 100.0 ± 0.0 | 100.0 ± 0.0 | 100.0 ± 0.0 |
| After 1 hr. | 97.5 ± 5.9 | 106.5 ± 11.3 | 114.4 ± 9.5 | 109.3 ± 6.3 |
| After 3 hrs. | 99.3 ± 4.8 | 101.7 ± 9.5 | 117.6 ± 13.9 | 110.2 ± 5.4 |
| After 5 hrs. | 94.2 ± 6.5 | 103.1 ± 6.5 | 117.6 ± 12.7 | 112.4 ± 7.0 |

|  | Control | Compound 2 (mg/kg, p.o.) 3 |
|---|---|---|
| Before administration | 100.0 ± 0.0 | 100.0 ± 0.0 |
| After 1 hr. | 107.5 ± 4.6 | 94.9 ± 14.3 |
| After 3 hrs. | 105.7 ± 7.7 | 93.6 ± 16.7 |
| After 5 hrs. | 111.7 ± 13.7 | 99.4 ± 9.0 |

|  | Control | Compound 3 (mg/kg, p.o.) 1 |
|---|---|---|
| Before administration | 100.0 ± 0.0 | 100.0 ± 0.0 |
| After 1 hr. | 103.2 ± 7.5 | 109.3 ± 5.7 |
| After 3 hrs. | 97.4 ± 4.6 | 109.5 ± 8.2 |
| After 5 hrs. | 98.5 ± 6.9 | 111.4 ± 5.6 |

|  | Control | Compound 4 (mg/kg, p.o.) 1 |
|---|---|---|
| Before administration | 100.0 ± 0.0 | 100.0 ± 0.0 |
| After 1 hr. | 97.9 ± 3.4 | 95.5 ± 8.2 |
| After 3 hrs. | 96.7 ± 3.9 | 106.2 ± 7.0 |
| After 5 hrs. | 92.8 ± 6.3 | 121.4 ± 9.5 |

|  | Control | Compound 5 (mg/kg, p.o.) 1 |
|---|---|---|
| Before administration | 100.0 ± 0.0 | 100.0 ± 0.0 |
| After 1 hr. | 107.5 ± 4.6 | 96.8 ± 4.4 |
| After 3 hrs. | 105.7 ± 7.7 | 109.4 ± 6.4 |
| After 5 hrs. | 111.7 ± 13.7 | 113.9 ± 15.4 |

|  | Control | Compound 6 (mg/kg, p.o.) 1 |
|---|---|---|
| Before administration | 100.0 ± 0.0 | 100.0 ± 0.0 |
| After 1 hr. | 107.5 ± 4.6 | 96.8 ± 4.4 |
| After 3 hrs. | 105.7 ± 7.7 | 109.4 ± 6.4 |
| After 5 hrs. | 111.7 ± 13.7 | 113.9 ± 15.4 |

According to the results of Test Example 1, Compounds 1 to 6 inhibited pre-micturition contractions (detrusor hyperreflexia) in the spinal cord-injured rats, but had no influence on their micturition contractions.

TEST EXAMPLE 2

Inhibitory Activity on Detrusor Instability

The experiment was carried out according to the method of Malmgren, et al. [J. Urol., Vol. 142, pp. 1134-1138 (1989)].

Female SD rats of 8 to 10 weeks of age (supplied by Japan SLC) were used in the test. Five to seven animals of these rats were put in each metal cage and reared by allowing them to freely take commercially available chow and water, in an animal room at room temperature between 19 and 25° C. and humidity between 30 and 70% under illumination for 12 hours (7:00 a.m.-7:00 p.m.) per day.

The rats were subjected to operation of partial urethral obstruction. Each animal was anesthetized by intraperitoneal administration of 50 mg/kg pentobarbital sodium (Dainippon Pharmaceutical Co., Ltd.), and the midline incision of the skin and muscle was made in the lower abdomen. A polyethylene tube (PE-20, Nippon Becton Dickinson Co., Ltd.) was inserted into urethra from the urethral to the bladder neck. After the proximal urethra was peeled and double-ligated, the polyethylene tube was pulled out to cause partial urethral obstruction. The incised part was sutured with a surgical silk thread. An antibiotic (ampicillin, Sigma Chemical Co.) was intramusclarly administered to the animals at a dose of 150 mg/kg.

Six weeks after the operation of the partial urethral obstruction, the rats with bladder hypertrophy were subjected to bladder catheterization. Under anesthesia with pentobarbital sodium, the bladder was exposed by midline incision of the abdomen. A polyethylene tube (PE-50, Nippon Becton Dickinson Co., Ltd.), which had a blunt end to protect tissue from injury, was filled with a physiological saline (Otsuka Pharmaceutical Co., Ltd.) and inserted from the bladder apex. The bladder catheter was fixed with a surgical silk ligature and indwelled. The other end of the catheter was exposed subcutaneously from the back of the neck, plugged and then fixed to the skin with a surgical thread.

Four to six days after the bladder catheterization, a cystometry test was performed. The rats were put in a Bollman cage (Natsume Seisakusho Co., Ltd.) and a three-way cock was connected to the bladder catheter, one end of the cock was connected to a pressure transducer (Nihon Kohden Corp.) and the other end was connected to a 50-mL syringe (Terumo Corp.) arranged to an infusion pump (Harvard Apparatus, Inc.) for physiological saline infusion. The intravesical pressure signal from the pressure transducer was amplified with a strain pressure amplifier (AP-601G, Nihon Kohden Corp.) connected thereto, and was recorded on a thermal array recorder (RTA-1200, Nihon Kohden Corp.) via a polygraph system (RMP-6008, Nihon Kohden Corp.) containing the above amplifier. Sixty to ninety minutes after the completion of the preparation for the measurement, intravesical infusion of a room temperature physiological saline at a flow rate of 10 mL/h was started and continued until the completion of the test, and the occurrence of micturition contractions and pre-micturition contractions were confirmed. The chart for 30 minutes after 3 hours from the commencement of the saline infusion was used as the values before the drug administration. Each of Compounds 1 to 3 was suspended in a 0.5 w/v % aqueous solution of methylcellulose at a concentration of 1 mg/mL. The suspension was further diluted with a 0.5 w/v % aqueous solution of methylcellulose to prepare a suspension or solution for the administration at the intended concentration. This was then orally administered to the animals at a volume of 1 mL/kg. The period of 1, 3 and 5 hours after the dosing was used as the measuring time after the administration of the solvent or a compound tested, and a duration of 15 minutes around each measuring time (45 to 75 minutes, 165 to 195 minutes and 285 to 315 minutes after the administration of the compound) was used as the measuring period.

Micturition contraction was used as an index of the voiding function and pre-micturition contraction was measure as an index of detrusor instability. The average for all micturition contraction values observed during each 30-minute measurement period and the average of the maximum pre-micturition contraction between respective micturition contractions were respectively regarded as the amplitude of micturition contractions and pre-micturition contractions at each measurement point. The values of both contractions were read from intravesical pressure waveforms recorded on a chart paper using a digitizer (KD3220, Graphtec Corporation) controlled by a computer (PC-9801NS/R, NEC), and saved as a WJ2 file on Lotus 1-2-3 R2.5J (Lotus). The WJ2 file was taken into Excel for Windows version 7.0 (Microsoft). The amplitude of pre-micturition contractions and micturition contractions were expressed as relative values when the values before the drug administration that were defined as 100, and the average± standard error was calculated for each group.

The values (%) of pre-micturition contractions after the administration of the solvent or compound are shown in Table 3 and the values (%) of micturition contractions are shown in Table 4.

TABLE 3

| | Control | Compound 1 (mg/kg, p.o.) | | |
| --- | --- | --- | --- | --- |
| | | 0.001 | 0.01 | 0.1 |
| Before administration | 100.0 ± 0.0 | 100.0 ± 0.0 | 100.0 ± 0.0 | 100.0 ± 0.0 |
| After 1 hr. | 105.5 ± 6.5 | 105.9 ± 7.8 | 59.5 ± 4.1*** | 55.8 ± 8.2*** |
| After 3 hrs. | 109.4 ± 14.8 | 100.3 ± 10.0 | 69.5 ± 4.4* | 66.2 ± 4.7* |
| After 5 hrs. | 103.3 ± 3.6 | 104.2 ± 10.2 | 67.8 ± 5.5** | 69.2 ± 7.4** |

| | Control | Compound 2 (mg/kg, p.o.) 3 |
| --- | --- | --- |
| Before administration | 100.0 ± 0.0 | 100.0 ± 0.0 |
| After 1 hr. | 107.5 ± 7.2 | 67.5 ± 7.9 |
| After 3 hrs. | 107.4 ± 7.8 | 66.9 ± 8.5 |
| After 5 hrs. | 108.2 ± 8.9 | 74.7 ± 7.6 |

| | Control | Compound 3 (mg/kg, p.o.) 10 |
| --- | --- | --- |
| Before administration | 100.0 ± 0.0 | 100.0 ± 0.0 |
| After 1 hr. | 107.5 ± 7.2 | 62.4 ± 7.1 |
| After 3 hrs. | 107.4 ± 7.8 | 49.1 ± 6.3 |
| After 5 hrs. | 108.2 ± 8.9 | 51.8 ± 3.5 |

*p < 0.05,
**p < 0.01,
***p < 0.001 (Comparison with the control group)
(n = 5-6: Dunnett test)

TABLE 4

| | Control | Compound 1 (mg/kg, p.o.) | | |
| --- | --- | --- | --- | --- |
| | | 0.001 | 0.01 | 0.1 |
| Before administration | 100.0 ± 0.0 | 100.0 ± 0.0 | 100.0 ± 0.0 | 100.0 ± 0.0 |
| After 1 hr. | 102.5 ± 3.5 | 99.3 ± 2.3 | 99.6 ± 1.2 | 106.2 ± 9.2 |
| After 3 hrs. | 104.4 ± 5.1 | 101.5 ± 3.3 | 92.6 ± 3.2 | 105.2 ± 9.6 |
| After 5 hrs. | 96.6 ± 3.2 | 98.7 ± 5.2 | 90.1 ± 4.3 | 100.1 ± 8.6 |

| | Control | Compound 2 (mg/kg, p.o.) 3 |
| --- | --- | --- |
| Before administration | 100.0 ± 0.0 | 100.0 ± 0.0 |
| After 1 hr. | 100.5 ± 2.9 | 104.5 ± 2.0 |
| After 3 hrs. | 97.5 ± 3.0 | 101.9 ± 5.9 |
| After 5 hrs. | 94.6 ± 2.6 | 100.9 ± 5.5 |

| | Control | Compound 3 (mg/kg, p.o.) 10 |
| --- | --- | --- |
| Before administration | 100.0 ± 0.0 | 100.0 ± 0.0 |
| After 1 hr. | 100.5 ± 2.9 | 96.8 ± 6.3 |
| After 3 hrs. | 97.5 ± 3.0 | 95.7 ± 4.7 |
| After 5 hrs. | 94.6 ± 2.6 | 92.2 ± 4.6 |

According to the test results, Compounds 1 to 3 inhibited pre-micturition contractions of the rats with bladder hypertrophy, but had no influence on the micturition contractions.

In Test Examples 1 and 2, Compounds (I) did not influence micturition contractions with voiding (no influence on voiding function), but inhibited pre-micturition contractions, which were irregular without voiding. These data demonstrate that Compounds (I) inhibit pre-micturition contractions (inhibit detrusor overactivity) and are useful as therapeutic agents for overactive bladder, and Compounds (I) or pharmaceutically acceptable salts thereof are considered to be useful as therapeutic agents for overactive bladder.

TEST EXAMPLE 3

Acute Toxicity Test

The test compound was administered orally or intraperitoneally to 3 animals per group of dd male mice (body weight: 20±1 g). The minimum lethal dose (MLD) value was obtained by observing mortality on the seventh day after the administration calculated.

As a result, MLD of Compound 1 was >1000 mg/kg by orally administration.

Compounds (I) and pharmaceutically acceptable salts thereof can be used as such or in various pharmaceutical forms. The pharmaceutical compositions of the present invention can be produced by uniformly mixing an effective amount of Compound (I) or a pharmaceutically acceptable salt thereof, as an active ingredient, with a pharmaceutically acceptable carrier. It is preferable that these pharmaceutical compositions are in a unit dose form suitable for administration such as oral administration or parenteral administration (including intravenous administration).

In the preparation of compositions for oral administration, any useful pharmaceutically acceptable carriers can be used. For example, liquid preparations for oral administration such as suspensions and syrups can be produced using water, sugars such as sucrose, sorbitol and fructose, glycols such as polyethylene glycol and propylene glycol, oils such as sesame oil, olive oil and soybean oil, antiseptics such as p-hydroxybenzoates, flavors such as strawberry flavor and peppermint, or the like. Capsules, tablets, powders and granules can be produced using excipients such as lactose, glucose, sucrose and mannitol, disintegrators such as starch and sodium alginate, lubricants such as magnesium stearate and talc, binders such as polyvinyl alcohol, hydroxypropyl cellulose and gelatin, surfactants such as fatty acid esters, plasticizers such as glycerin, or the like. Tablets and capsules are the most useful unit dose forms for oral administration because of the easiness of administration. Solid pharmaceutical carriers are used for the production of tablets and capsules.

Injections can be prepared using, for example, carriers comprising distilled water, a salt solution, a glucose solution or a mixture of salt water and a glucose solution. They are prepared as solutions, suspensions or dispersed solutions using appropriate auxiliaries according to conventional methods.

Compounds (I) or pharmaceutically acceptable salts thereof can be administered orally in the above pharmaceutical forms or parenterally as an injection or the like. The effective dose and administration schedule vary depending upon the mode of administration, the age, body weight and condition of: a patient, or the like, but they are usually administered in a dose of 1 to 900 mg/60 kg/day, preferably 1 to 200 mg/60 kg/day.

Certain embodiments of the present invention are illustrated in the following examples.

BEST MODES FOR CARRYING OUT THE INVENTION

EXAMPLE 1

Tablets

Tablets having the following compositions were prepared according to a conventional method.

Compound 1 (250 g), mannitol (1598.5 g), sodium starch glycolate (100 g), light silicic acid anhydride (10 g), magnesium stearate (40 g) and yellow iron oxide (1.5 g) were mixed according to a conventional method. The resulting mixture was compressed using a tableting machine within 8 mm diameter punch and die (Purepress Correct-12, Kikusui Seisakusho, Ltd.) to prepare tablets each containing 25 mg of the active ingredient.

The formulation is shown in Table 5.

TABLE 5

| Formulation | Compound 1 | 25 mg |
|---|---|---|
| | Mannitol | 159.85 mg |
| | Sodium starch glycolate | 10 mg |
| | Light silicic acid anhydride | 1 mg |
| | Magnesium stearate | 4 mg |
| | Yellow iron oxide | 0.15 mg |
| | | 200 mg |

EXAMPLE 2

Capsules

Capsules having the following composition were prepared according to a conventional method.

Compound 1 (500 g), lactose (300 g), light silicic acid anhydride (100 g) and sodium lauryl sulfate (100 g) were mixed according to a conventional method. The resulting mixture was encapsulated in hard capsules No. 1 (content: 100 mg/capsule) using a capsule filler (LZ-64, Zanasi) to prepare capsules each containing 50 mg of the active ingredient.

The formulation is shown in Table 6.

TABLE 6

| Formulation | Compound 1 | 50 mg |
|---|---|---|
| | Lactose | 30 mg |
| | Light silicic acid anhydride | 10 mg |
| | Sodium lauryl sulfate | 10 mg |
| | | 100 mg |

EXAMPLE 3

Injection

An injection having the following composition was prepared according to a conventional method.

Compound 1 (1 g) was dissolved in 100 g of purified soybean oil, and 12 g of purified egg yolk lecithin and 25 g of glycerin for injection were added thereto. The resulting mixture was made up to 1000 mL with distilled water for injection, kneaded and emulsified according to a conventional method. The obtained dispersed solution was aseptically filtered using a 0.2 μm disposable membrane filter and aseptically packed in glass vials in 2 mL portions to prepare an injection containing 2 mg of the active ingredient per vial.

The formulation is shown in Table 7.

TABLE 7

| Formulation | Compound 1 | 2 mg |
|---|---|---|
| | Purified soybean oil | 200 mg |
| | Purified egg yolk lecithin | 24 mg |
| | Glycerin for injection | 50 mg |
| | Distilled water for injection | 1.72 mL |
| | | 2.00 mL |

INDUSTRIAL APPLICABILITY

The present invention provides a therapeutic agent for overactive bladder comprising, as an active ingredient, a tricyclic compound or a pharmaceutically acceptable salt thereof.

The invention claimed is:

1. A method for treating overactive bladder, comprising administering to a patient suffering from overactive bladder an effective amount of a tricyclic compound represented by formula (Ia):

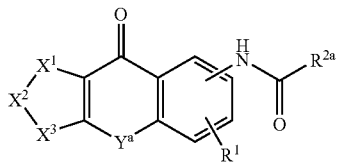

wherein $R^1$ represents a hydrogen atom;

$X^1$—$X^2$—$X^3$ represents S—$CR^7$=$CR^8$ (wherein $R^7$ and $R^8$ represent a hydrogen atom);

$Y^a$ represents —$CH_2SO_2$—; and $R^{2a}$ represents formula (II):

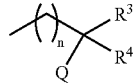

wherein n is 0 or 1; $R^3$ and $R^4$ independently represent a hydrogen atom or substituted or unsubstituted lower alkyl; and Q represents hydroxy or substituted or unsubstituted lower alkoxy, or a pharmaceutically acceptable salt thereof.

2. The method for treating overactive bladder according to claim 1, wherein n is 0.

3. The method for treating overactive bladder according to claim 2, wherein $R^3$ is methyl, $R^4$ is trifluoromethyl, and Q is hydroxy.

4. The method for treating overactive bladder according to claim 1, wherein $R^{2a}$ is formula (III):

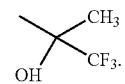

* * * * *